United States Patent [19]

Goetz et al.

[11] Patent Number: 4,968,831
[45] Date of Patent: Nov. 6, 1990

[54] PREPARATION OF α-KETOCARBOXYLIC ESTERS

[75] Inventors: Norbert Goetz, Worms; Wolfgang Hoelderich, Frankenthal; Leopold Hupfer, Friedelsheim, all of Fed. Rep. of Germany

[73] Assignee: BASF Aktiengesellschaft, Ludwigshafen, Fed. Rep. of Germany

[21] Appl. No.: 323,861

[22] Filed: Mar. 15, 1989

[30] Foreign Application Priority Data

Mar. 15, 1989 [DE] Fed. Rep. of Germany ....... 3808512

[51] Int. Cl.$^5$ ............................................. C07C 69/76
[52] U.S. Cl. ...................................................... 560/51
[58] Field of Search ............................................ 560/51

[56] References Cited

U.S. PATENT DOCUMENTS 4,016,196 4/1977 Kogure et al. ........................ 560/51

FOREIGN PATENT DOCUMENTS 100117 8/1984 European Pat. Off. .

*Primary Examiner*—Paul J. Killos
*Attorney, Agent, or Firm*—Keil & Weinkauf

[57] ABSTRACT

α-Ketocarboxylic esters

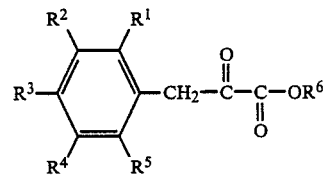

where $R^1$, $R^2$, $R^3$, $R^4$ and $R^5$ are identical to or different from one another and are each hydrogen or straight-chain or branched alkyl, alkenyl, hydroxyl, alkoxy cycloalkyl or halogen and $R^6$ is unbranched lower alkyl, are prepared by reacting glycidic esters of the formula

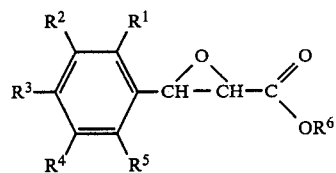

where $R^1$, $R^2$, $R^3$, $R^4$, $R^5$ and $R^6$ are each as defined above, in the presence of zeolites or phosphates and/or phosphoric acid or boric acid on a carrier material and/or acidic metal oxides as catalysts and are used for preparing phenylacetic esters.

8 Claims, No Drawings

PREPARATION OF α-KETOCARBOXYLIC ESTERS

The present invention relates to a process for preparing α-ketocarboxylic esters from glycidic esters in the presence of zeolites and/or phosphates and/or phosphoric acid or boric acid on carrier material and/or acidic metal oxides and to the use of these α-ketocarboxylic esters for preparing phenylacetic esters over the same catalysts.

The glycidic ester intermediates used can be prepared in a simple manner from carbonyl compounds, for example aldehydes and ketones, and α-chlorocarboxylic esters. This provides a very widely applicable method with which almost any desired substitution pattern can be obtained.

The synthesis of α-ketocarboxylic acids and esters was previously very complicated, involving for example Grignard reactions with oxalic esters.

The standard process for preparing phenylacetic esters comprises the reaction of benzyl halides with potassium cyanide to give benzyl cyanides and the hydrolysis thereof to phenylacetic esters, a multistage process where highly toxic potassium cyanide has to be used.

As regards the subsequent use not only of the α-ketocarboxylic esters but also of the phenylacetic esters, there are a number of options; α-ketocarboxylic acids and derivatives thereof can be used for preparing herbicidal triazinones (EP 58,885, DE-A- No. 3,106,707) or for isolating L-amino acids (DE-A- No. 3,614,586).

It is known that epoxys can be rearranged in the presence of zeolites to carbonyl compounds.

EP No. 100,117 describes the reaction of styrene oxide and of styrene oxides with alkyl or alkoxy substitution on the aromatic ring over a titanium-containing zeolite in the liquid phase at from 30° to 100° C. to give phenylacetaldehydes. The catalyst used for this purpose has to be expensively prepared from costly high-purity starting materials such as tetraalkyl orthosilicate, tetraalkyl orthotitanate and tetrapropylammonium hydroxide. High conversions are only obtained if the reaction is carried out on solvents such as methanol acetone at from 30° to 100° C. at the liquid phase with residence times of from 1 to 1.5 hours. This creates increased distillation and operating expenses. Furthermore, the reaction over titanium-containing zeolites is only possible in the case of styrene oxide and alkylated or alkoxylated styrene oxides.

There is other prior art concerning the rearrangement of epoxys to carbonyl compounds. Cyclodecanone, for example, is obtained from epoxycyclododecane over Pd- or Rd-doped Al₂O₃ (Neftekhimiya 16 (1976), 250–254). In this paper it is expressly pointed out that zeolites are unsuitable for this reaction. Similarly, the use of A-zeolites for the rearrangement of butylene oxide to butyraldehyde (55–72%) has been described (Hokkaido Daigaku Kogarubu Hokoku 67 (1973), 171–178). The selectivity leaves something to be desired. Moreover, the A-zeolite catalyst, once deactivated by coking, is difficult to regenerate, since the temperatures of about 500° C. required for this purpose destroy the crystal structure of this zeolite. Furthermore, to convert propylene oxide into acetone or propionaldehyde over alkali metal doped X-zeolites it is necessary to work in the absence of strongly acidic centers (Waseda Daigaku Rikogaku Kenkyusho Hokoku 67 (1974), 26–29).

It is an object of the present invention to prepare α-ketocarboxylic esters and phenylacetic esters in a simple manner from inexpensive glycidic esters, ideally with maximum conversion, selectivity and catalyst life.

We have found that this object is achieved by preparing α-ketocarboxylic esters of the formula (I)

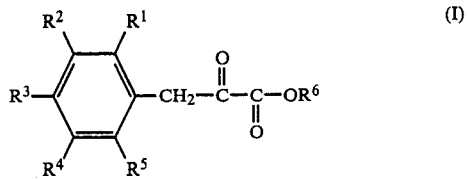

where $R^1$, $R^2$, $R^3$, $R^4$ and $R^5$ are identical to or different from one another and are each hydrogen or straight-chain or branched alkyl, alkenyl, hydroxyl, alkoxy, cycloalkyl or halogen and $R^6$ is lower alkyl, by reacting glycidic esters of the formula II

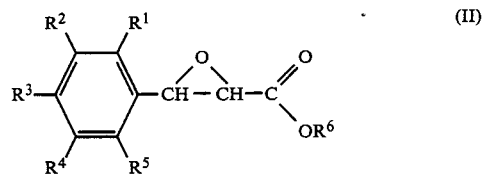

where $R^1$, $R^2$, $R^3$, $R^4$, $R^5$ and $R^6$ are each as defined above, in the presence of zeolites and/or phosphates and/or phosphonic acid or boric acid on carrier material and/or acidic metal oxides as catalysts.

The α-ketocarboxylic esters of the formula I can be used for preparing phenylacetic esters of the formula (III)

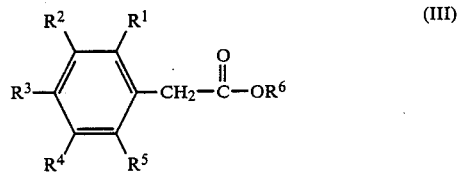

by decarbonylation at above 300° C. in the presence of the abovementioned catalysts.

It is also possible to convert glycidic esters of the formula (II) in one stage directly into the phenylacetic esters of the formula (III) without isolating the α-ketocarboxylic esters of the formula (I) if the reaction temperature is equal to or higher than 350° C.

Suitable $R^1$, $R^2$, $R^3$, $R^4$ and $R^5$ of the formula (I), which may be identical to or different from one another, are hydrogen and straight-chain or branched alkyl of from 1 to 8 carbon atoms, in particular of from 1 to 4 carbon atoms, such as methyl, ethyl, n/i-propyl, n/i/t-butyl or n-hexyl, and straight-chain or branched alkenyl of from 1 to 8 carbon atoms, in particular of from 1 to 4 carbon atoms, such as ethenyl, propenyl or butenyl, and hydroxyl, and hydroxyl, and straight-chain or branched alkoxy of from 1 to 8 carbon atoms, in particular of from 1 to 4 carbon atoms, such as methoxy, ethoxy, propoxy or butoxy, and cycloalkyl such as cyclopentyl or cyclohexyl, cyclohexenyl, halogen, such as F or Cl, trifluoromethyl, trichloromethyl, trifluoromethoxy, monofluoromethyl, fluoroethyl and fluoropropyl.

$R^6$ is unbranched lower alkyl, in particular of from 1 to 4 carbon atoms, such as methyl, ethyl, n-propyl or n-butyl.

The catalysts used for the process according to the invention are acidic zeolitic catalysts. Zeolites are crystalline aluminosilicates which possess a highly ordered structure comprising a rigid three-dimensional network of $SiO_4$ and $AlO_4$ tetrahedra joined together by common oxygen atoms. The ratio of the Si and Al atoms: oxygen is 1:2. The electrovalence of the aluminum-containing tetrahedra is balanced by the inclusion of cations, for example an alkali metal or hydrogen ion, in the crystal. Cation exchange is possible. The spaces between the tetrahedra are occupied prior to dehydration by drying or calcination by water molecules. In zeolites, the aluminum in the lattice may also be replaced by other elements such as B Ga, Fe, Cr, V, As, Sb, Bi or Be or mixtures thereof, or the silicon may be replaced by a tetravalent element such as Ge, Ti, Zr or Hf.

The catalysts used for the processes according to the invention are in particular zeolites of the mordenite group or narrow-pored zeolites of the erionite or chabasite type or zeolites of the faujasite type, for example Y-, X- or L-zeolites. This group of zeolites also includes the ultrastable zeolites of the faujasite type, i.e. dealuminized zeolites. Processes for preparing such zeolites are described in Catalysis by Zeolites, volume 5 of Studies in Surface Science and Catalysis ed. B. Imelik et al., Elsevier Scientific Publishing Comp., 1980, page 203, and Crystal Structures of Ultra-stable Faujasites, Advances in Chemistry Series No. 101, American Chemical Society Washington DC, pages 226 et seq. (1971), and in U.S. Pat. No. 4,512,961.

It is advantageous to use zeolites of the pentasil type. Their common building block is a five-membered ring composed of $SiO_4$ tetrahedra. They are characterized by a high $SiO_2/Al_2O_3$ ratio and by pore sizes between those of the zeolites of Type A and those of Type X or Y.

These zeolites may have different chemical compositions. They are aluminosilicate, borosilicate, iron silicate, beryllium silicate, gallium silicate, chromium silicate, arsenic silicate, antimony silicate and bismuth silicate zeolites or mixtures thereof and aluminogerminate, borogerminate, gallium germinate and iron germinate zeolites or mixtures thereof. Specifically, aluminosilicate, borosilicate and iron silicate zeolites of the pentasil type are suitable for the process according to the invention. The aluminosilicate zeolite is prepared for example from an aluminum compound, preferably $Al(OH)_3$ or $Al_2(SO_4)_3$, and from a silicon component, preferably finely divided silicon dioxide, in an aqueous amine solution in particular in polyamines such as 1,6-hexanediamine or 1,3-propane-diamine or triethylenetetramine solution, with or in particular without the addition of alkali metal or alkaline earth metal at from 100° to 220° C. under autogenous pressure. This also includes the isotactic zeolites described in EP No. 34,727 and EP No. 46,504. The aluminosilicate zeolites obtained have an $SiO_2/Al_2O_3$ ratio of from 10 to 40,000, depending on the choice of starting quantities. It is also possible to synthesize such aluminosilicate zeolites in an etherial medium, such as diethylene glycol, dimethyl ether, in an alcoholic medium such as methanol or 1,4-butanediol, or in water.

The borosilicate zeolite is synthesized for example at from 90° to 200° C. under autogenous pressure by reacting a boron compound, for example $H_3BO_3$, with a silicon compound, preferably finely divided silicon dioxide, in an aqueous amine solution, in particular in 1,6-hexane-diamine or 1,3-propanediamine or triethylenetetramine solution, with or in particular without the addition of an alkali metal or alkaline earth metal. Isotactic zeolites as described in EP No. 34,727 and EP No. 46,504 are also suitable. These borosilicate zeolites can also be prepared by carrying out the reaction not in an aqueous amine solution but in an ethereal solution, for example in diethylene glycol dimethyl ether, or in an alcoholic solution, for example 1,6-hexanediol.

The iron silicate zeolite is obtained for example from an iron compound, preferably $Fe_2(SO_4)_3$, and a silicon compound, preferably finely divided silicon dioxide, in an aqueous amine solution, in particular 1,6-hexanediamine, with or without the addition of an alkali metal or alkaline earth metal, at from 100° to 220° C. under autogenous pressure.

The usable high-silicon zeolites ($SiO_2/Al_2O_3 \geq 10$) include the ZSM types, ferrierite, Nu-1 and Silicalit ® molecular seive, a silica polymorph).

The aluminosilicate, borosilicate and iron silicate zeolites thus prepared, after they have been isolated, at from 100° to 160° C., preferably at 110° C., and calcined at from 450° to 550° C., preferably at 500° C., can be molded with a binder in a ratio of from 90:10 to 40:60% by weight into extrudates or tablets. Suitable binders are various aluminum oxides, preferably boehmite, amorphous aluminosilicates having an $SiO_2/Al_2O_3$ ratio of from 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$ and clay. After molding, the extrudates or pellets are dried at 110° C. over 16 h and calcined at 500° C. over 16 h.

Advantageous catalysts are also obtained on molding the isolated aluminosilicate or borosilicate zeolite directly after drying and subjecting it to a calcination only after molding. The synthesized aluminosilicate and borosilicate zeolites can be used in the pure form, without binder, as extrudates or tablets, in which case the extruding or peptizing aids used are for example ethylcellulose, stearic acid, potato starch, formic acid, oxalic acid, acetic acid, nitric acid, ammonia, amines, silicoesters and graphite or mixtures thereof.

If the zeolite, owing to its manner of preparation, is present not in the catalytically active, acidic H-form but for example in the Na-form, it can be completely or partially converted into the desired H-form by ion exchange, for example with ammonium ions, and subsequent calcination or by treatment with acids.

If in the course of the use of the zeolitic catalysts deactivation occurs due to the deposition of coke, it is advisable to regenerate the zeolites by burning off the coke deposit with air or with an air/$N_2$ mixture at from 400° to 550° C., preferably at 500° C. This restores the zeolites to their initial activity.

By partial precoking it is possible to set the activity of the catalyst for optimum selectivity in respect of the desired reaction product.

To obtain maximum selectivity, high conversion and long catalyst lives, it is advantageous to modify the zeolites. A suitable modification of the catalyst comprises for example doping the unmolded or molded zeolites with metal salts by ion exchange or impregnation. The metals used are alkali metals such as Li, Cd or K, alkaline earth metals such as Mg, Ca or Sr, metals of main groups 3, 4 and 5 such as Al, Ga, Ge, Sn, Pb or Bi, transition metals of subgroups 4 to 8 such as Ti, Zr, V, Nb, Cr, Mo, W, Mn, Re, Fe, Ru, Os, Co, Rh, Sr, Ni, Pd or Pt, transition metals of subgroups 1 and 2 such as Cu, Ag or Zn, or rare earth metals such as La, Ce, Pr, Nd, Fr, Yb or U.

Advantageously, the doping is carried out by introducing the molded zeolites initially in a riser tube and passing an aqueous or ammoniacal solution of a halide or a nitrate of a metal as described over it at from 20° to 100° C. Such an ion exchange can be effected for example, on the hydrogen, ammonium and alkali metal form of the zeolite. A further way of applying metal to the zeolite comprises impregnating the zeolitic material with a halide, a nitrate or an oxide of the metals described in aqueous, alcoholic or ammoniacal solution. Not only ion exchange but also impregnation are followed by at least one drying operation, alternatively by a further calcination.

A possible embodiment comprises dissolving $Cu(NO_3)_2 \times 3H_2O$ or $Ni(NO_3)_2 \times 6H_2O$ or $Ce(NO_3)_3 \times 6H_2O$ or $La(NO_3)_2 \times 6H_2O$ or $Cs_2CO_3$ in water. The molded or unmolded zeolite is impregnated with this solution for a certain time, say 30 minutes. The supernatant solution is stripped of water in a rotary evaporator. Thereafter the impregnated zeolite is dried at about 150° C. and calcined at about 550° C. This impregnation can be carried out repeatedly in succession in order to obtain the desired metal content.

It is also possible to prepare an aqueous $Ni(CO_3)_2$ solution of ammoniacal $Pd(NO_3)_2$ solution and to suspend the pure pulverulent zeolites therein at from 40° to 100° C. by stirring for about 24 hours. Following filtration, drying at about 150° C. and calcination at about 500° C., the zeolitic material thus isolated can be further processed with or without binders into extrudates, pellets or fluidizable material.

An ion exchange on the zeolites present in the H-form or ammonium form or alkali metal form can be effected by introducing the zeolites initially in extrudates or pellets into a column and passing an aqueous $Ni(NO_3)_2$ solution or ammoniacal $Pd(NO_3)_2$ solution at a slightly elevated temperature of from 30° to 80° C. over it in a cycle for from 15 to 20 hours. This is followed by washing with water, drying at about 150° C. and calcining at about 550° C. With some metal-doped zeolites such as the Pd-, Cu- or Ni-doped zeolites, an aftertreatment with hydrogen is advantageous.

A further modifying technique comprises subjecting the zeolitic material, molded or unmolded, to a treatment with acids such as hydrochloric acid, hydrofluoric acid and phosphoric acid and/or steam. An advantageous procedure is to treat zeolites in powder form with 1 N phosphoric acid at 80° C. for 1 hour, washing with water, drying at 110° C. over 16 h and calcining at 500° C. over 20 h.

In another procedure, zeolites are treated before or after molding with binders with from 3 to 25% strength by weight, in particular from 12 to 20% strength by weight, aqueous hydrochloric acid at from 60° to 80° C., for example from 1 to 3 hours. Thereafter the zeolite thus treated is washed with water, dried and calcined at from 400° to 500° C.

A particular form of the acid treatment comprises treating the zeolitic material before it is molded with from 0.001 N to 2 N, preferably from 0.05 N to 0.5 N, hydrofluoric acid for from in general 0.5 to 5, preferably from 1 to 3, hours at an elevated temperature, by refluxing. After the zeolitic material is isolated by filtration and washed, it is advantageously dried at from 100° to 160° C. and calcined at from 450° to 600° C. In another preferred form of the acid treatment, the zeolitic material, after molding with binder, is treated at elevated temperatures, advantageously at from 50° to 90° C., preferably at from 60° to 80° C., with from 12 to 20% strength by weight hydrochloric acid for from 0.5 to 5 hours. Thereafter the zeolitic material is washed and advantageously dried at from 100° to 160° C. and calcined at from 450° to 600° C. An HF treatment may also be followed by an HCl treatment.

In another procedure, zeolites can be modified by applying phosphorus compounds, such as trimethoxyphosphate, trimethoxyphosphine or primary, secondary or tertiary sodium phosphate. The treatment with primary sodium phosphate has proved particularly advantageous. Here the zeolites are impregnated in extruded, tablet or fluidized form with aqueous $NaH_2PO_4$ solution, dried at 110° C. and calcined at 500° C.

Further catalysts for the process are phosphates, in particular aluminum phosphates, silicon aluminum phosphates, silicon iron aluminum phosphates, cerium phosphates, zirconium phosphates, boron phosphates, iron phosphates and mixtures thereof.

Aluminum phosphate catalysts used for the process are in particular hydrothermally synthesized aluminum phosphates which have a zeolite structure.

Hydrothermally synthesized aluminum phosphates are for example APO-5, APO-9, APO-11, APO-12, APO-14, APO-21, APO-25, APO-31 and APO-33. Syntheses of these compounds are described in EP No. 132,708, U.S. Pat. No. 4,301,440 and U.S. Pat. No. 4,473,663.

$AlPO_4$-5 (APO-5) for example is synthesized by homogeneously mixing orthophosphoric acid with pseudoboehmite (Catapol S8 ®) in water, adding tetrapropylammonium hydroxide, and then reacting in an autoclave at about 150° C. under autogenous pressure for from 20 to 60 hours. The $AlPO_4$ is filtered off, dried at from 100° to 160° C. and calcined at from 450° to 550° C.

$AlPO_4$-9 (APO-9) is synthethized from orthophosphoric acid and pseudoboehmite in aqueous DABCO solution (1,4-diazabicyclo[2.2.2]octane) at about 200° C. under autogenous pressure in the course of from 200 to 400 hours.

$AlPO_4$-21 (APO-21) is synthesized from orthophosphoric acid and pseudoboehmite in aqueous pyrrolidone solution at from 150° to 200° C. under autogenous pressure in the course of 50 to 200 hours.

The silicon aluminum phosphates used for the process according to the invention are for example SAPO-5, SAPO-11, SAPO-31 and SAPO-34. The synthesis of these compounds is described in EP No. 103,117 and U.S. Pat. No. 4,440,871. SAPOs are prepared by crystallization from aqueous mixture at from 100° to 250° C. under autogenous pressure in the course of from 2 hours to 2 weeks, during which the reaction mixture comprising a silicon component, an aluminum component and a phosphorus component is converted in aqueous organoamine solutions.

SAPO-5 is obtained by mixing $SiO_2$ suspended in aqueous tetrapropylammonium hydroxide solution with an aqueous suspension of pseudoboehmite and orthophosphoric acid and subsequent reaction at 150°–200° C. for from 20 to 200 hours under autogenous pressure in a stirred autoclave. The powder is filtered off, dried at from 110° to 160° C. and calcined at from 450° to 550° C.

Phosphate catalysts used for the process also include precipitated aluminum phosphates. Such aluminum phosphate is prepared for example by dissolving 92 g of diammonium hydrogenphosphate in 700 ml of water. 260 g of Al(NO$_3$)$_3 \times$ H$_2$O in 700 ml of water are added dropwise over 2 hours, during which the pH is maintained at pH 8 by the simultaneous addition of 25% strength NH$_3$ solution. The resulting precipitate is subsequently stirred for 12 hours, and then filtered off with suction and washed. It is dried at 60° C. over 16 h.

Suitable boron phosphates for the process according to the invention can be prepared for example by mixing and kneading concentrated boric acid and phosphoric acid and subsequent drying and calcination in an inert gas, air or steam atmosphere at from 250° to 650° C., preferably at from 300° to 500° C.

These phosphates may also be treated with modifying components as described above for zeolites by impregnation (soaking or spraying) or in some cases by ion exchange. As with the zeolite catalysts, modification with acids is also possible.

Suitable acidic catalysts are for example the acidic oxides of elements of main groups III and IV and also subgroups IV, V and VI of the periodic table, in particular oxides such as silicon dioxide in the form of silica gel, diatomaceous earth or quartz, and also titanium dioxide, zirconium dioxide, phosphorus oxides, vanadium oxides, niobium oxides, boron oxides, chromium oxides, molybdenum oxides, tungsten oxides or pumice or mixtures of these oxides. These oxides can also be doped by applying modifying components as described above for the zeolite catalysts. Another possible modifying technique is as with the zeolite catalysts a treatment with acids.

It is possible to use catalysts impregnated with phosphoric acid or boric acid. Phosphoric acid or boric acid is applied for example to SiO$_2$, Al$_2$O$_3$ or pumice carrier material, for example by impregnating or spraying. A catalyst which contains phosphoric acid can be obtained for example by impregnating SiO$_2$ with H$_3$PO$_4$, NaH$_2$PO$_4$ or Na$_2$HPO$_4$ solution and subsequent drying or calcination. However, phosphoric acid can also be sprayed together with silica gel in a spray tower; this is followed by a drying step and usually by a calcination. Phosphoric acid can also be sprayed onto the carrier material in an impregnating mill.

The catalysts described here can be optionally used as from 2 to 4 mm extrudates or as tablets from 3 to 5 mm in diameter or as chips from 0.1 to 0.5 mm in particle size or in fluidizable form.

The conversion according to the invention is preferably carried out in the gas phase at from 100° to 500° C., preferably at from 200° to 350° C., in particular at from 250° to 300° C., under a weight hourly space velocity (WHSV) of from 0.1 to 20 h$^{-1}$, preferably of from 0.5 to 5 h$^{-1}$, of g of starting material per g of catalyst per hour. The reaction can be carried out in a fixed bed or alternatively in a fluidized bed.

It is also possible to carry out the reaction in the liquid phase (by the suspension, trickle bed or liquid phase procedure) at from 50° to 200° C.

The process can be carried out under atmospheric pressure, under reduced pressure or under superatmospheric pressure, batchwise or preferably continuously.

Sparingly volatile or solid starting materials are used in dissolved form, for example in THF, toluene or petroleum ether solution. In general, a dilution of starting materials with the solvents or with inert gases such as N$_2$, Ar or H$_2$O vapor is possible.

After the reaction, the products formed are isolated from the reaction mixture in a conventional manner, for example by distillation; unconverted starting mixture is recycled, where appropriate.

EXAMPLES 1 TO 15

The reactions are carried out in the gas phase under isothermal conditions in a tubular reactor (coil, 0.6 cm internal diameter, 90 cm in length) for not less than 6 hours. The reaction products are separated off and characterized in a conventional manner. The quantitative determination of the reaction products and the starting materials is done by gas chromatography.

Catalyst A

The borosilicate zeolite of the pentasil type is prepared in a hydrothermal synthesis from 640 g of finely divided SiO$_2$, 122 g of H$_3$BO$_3$ and 8000 g of an aqueous 1,6-hexadiamine solution (mixture 50:50% by weight) at 170° C. under autogenous pressure in a stirred autoclave. After filtration and washing, the crystalline reaction product is dried at 100° C. over 24 h and calcined at 500° C. over 24 h. This borosilicate zeolite is composed of 94.2% by weight SiO$_2$ and 2.3% by weight of B$_2$O$_3$.

This material is used to produce by molding with a molding aid 2 mm extrudates which are dried at 110° C. over 16 h and calcined at 500° C. over 24 h.

Catalyst B

An aluminosilicate zeolite of the pentasil type is prepared under hydrothermal conditions under autogenous pressure and at 150° C. from 65 g of finely divided SiO$_2$ and 20.3 g of Al$_2$(SO$_4$)$_3 \times$ 18 H$_2$O in 1 kg of an aqueous 1,6-hexanediamine solution (mixture 50:50% by weight) in a stirred autoclave. The crystalline reaction product is filtered off, washed, dried at 110° C. over 24 h and calcined at 500° C. over 24 h. This aluminosilicate zeolite contains 91.6% by weight of SiO$_2$ and 4.6% by weight of Al$_2$O$_3$. The catalyst is molded with a molding aid into 2 mm extrudates, dried at 110° C. over 16 h and calcined at 500° C. over 24 h.

Catalyst C

Catalyst C is obtained by impregnating the extrudates of Catalyst A with an aqueous Cs$_2$CO$_3$ solution, then drying at 130° C. over 2 h and calcining at 540° C. over 2 h. The Cs content is 0.6% by weight.

Catalyst D

Catalyst D is prepared in the same way as Catalyst C, except that Cs$_2$CO$_3$ is replaced by Ce(NO$_3$)$_2$. The Ce content is 1.8% by weight.

Catalyst E

The synthesis of AlPO$_4$-5 (APO-5) is effected by stirring together 200 g of a 95% strength phosphoric acid dissolved in 325 g of H$_2$O, 136 g of boehmite and 678 g of tetrapropylammonium hydroxide (30% strength) and subsequent reaction at 150° C. under autogenous pressure for 43 hours. The product dried at 120° C. and calcined at 500° C. over 16 h contains 46.5% by weight of P$_2$O$_5$ and 45.5% by weight of Al$_2$O$_3$. This AlPO$_4$-5 is molded with boehmite in a weight ratio of 60:40 and 2 mm extrudates, dried at 110° C. and calcined at 500° C. over 16 h.

Catalyst F

Silicon aluminum phosphate-5 (SAPO-5) is prepared from a mixture of 200 g of 98% strength phosphoric acid, 136 g of boehmite, 60 g of silica sol (30% strength), 287 g of tripropylamine and 587 g of $H_2O$. This mixture is reacted at 150° C. under autogenous pressure for 168 hours. The crystalline product is filtered off, dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with a molding aid into 3 mm extrudates, dried at 120° C. and calcined at 500° C.

Catalyst G

Commercial zirconium phosphate $Zr_3(PO_4)_4$ molded in pure form.

Catalyst H $BPO_4$ is prepared by adding 49 g of $H_3BO_3$ together with 117 g of $H_3PO_4$ (75% strength) to a kneader, evaporating off excess water and molding the reaction product into 3 mm extrudates. These extrudates are dried at 100° C. and calcined at 350° C. Catalyst H contains 8.77% by weight of B and 28.3% by weight of P.

Catalyst I $SiO_2$ commercially available as D 11-10 ®.

The experimental results obtained for these catalysts under which experimental conditions are summarized in Tables 1 and 2.

EXAMPLE 16

100 ml of methyl p-tert-butylphenylglycidate per hour are passed in the presence of 200 l/h of $N_2$ at 180° C. over 1 l of catalyst A accomodated in a tubular reactor electrically heated from the outside. The gaseous reaction products are condensed and worked up and characterized in a conventional manner. The preparation of pure methyl ester of 3-[p-tert-butyl]phenylpyruvic acid is possible by conventional distillation. A yield of 91.8% is isolated.

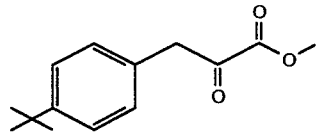

bp = 135° C./0.3 mbar
white crystals

EXAMPLE 17

100 ml of the methyl ester of 3-[p-tert-butyl]-phenylpyruvic acid are vaporized in the presence of 200 l/h of $N_2$ and passed at 350° C. over 1 l of catalyst A (apparatus as in Example 16). Conventional working up reveals a conversion of 31% and a selectivity of 83% in respect of methyl p-tert-butylphenylacetate.

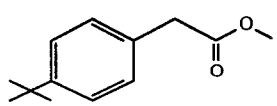

bp = 96° C./0.4 mbar

EXAMPLE 18

Example 16 is repeated, except that the temperature employed is 350° C. A mixture of methyl 3-[p-tert-butyl]-phenylpyruvate and methyl p-tert-butylphenylacetate in a ratio of 65:35 is found.

TABLE 1

Conversion of methyl phenylglycidate (1) into methyl 3-phenylpyruvate (2)

| | Examples | | | | | | | | |
|---|---|---|---|---|---|---|---|---|---|
| | 1 | 2 | 3 | 4 | 5 | 6 | 7 | 8 | 9 |
| Catalysts | A | B | C | D | E | F | G | H | I |
| Temperature °C. | 200 | 200 | 200 | 200 | 200 | 200 | 200 | 200 | 200 |
| WHSV $h^{-1}$ | 3.0 | 3.0 | 3.0 | 3.0 | 3.0 | 3.0 | 3.0 | 3.0 | 3.0 |
| Conversion of (1) | 100 | 100 | 100 | 100 | 100 | 100 | 100 | 100 | 100 |
| Selectivity for (2) | 92.5 | 88.1 | 93.7 | 89.7 | 78.3 | 86.9 | 81.5 | 84.8 | 80.3 |

TABLE 2

Conversion of substituted methyl phenylglycidates of the formula (II) into substituted methyl 3-phenylpyruvates of the formula (I)

| | Example | | | | | |
|---|---|---|---|---|---|---|
| | 10 | 11 | 12 | 13 | 14 | 15 |
| Substituent on aromatics | 4-fluoro | 4-methyl | 4-methoxy | 4-trifluoromethyl | 4-t-butyl | 1-methyl-4-fluoro |
| catalyst | A | A | A | A | A | A |
| temp. °C. | 200 | 200 | 200 | 200 | 200 | 200 |
| WHSV $h^{-1}$ | 3.0 | 3.0 | 3.0 | 3.0 | 3.0 | 3.0 |
| Conversion of (II) | 100 | 100 | 100 | 100 | 100 | 100 |
| Selectivity for (I) | 87.5 | 93.7 | 92.5 | 92.3 | 90.3 | 91.0 |

We claim:
1. A process for preparing an α-ketocarboxylic ester of the formula (I)

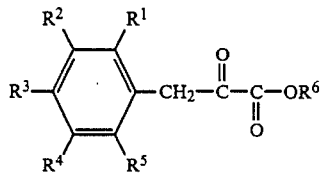 (I)

where $R^1$, $R^2$, $R^3$, $R^4$ and $R^5$ are identical to or different from one another and are each hydrogen or straight-chain or branched alkyl, alkenyl, hydroxyl, alkoxy, cycloalkyl or halogen and $R^6$ is unbranched lower alkyl, which comprises reacting a glycidic ester of the formula (II)

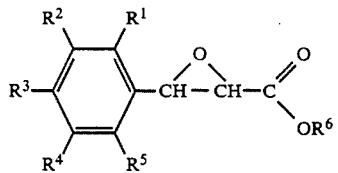 (II)

where $R^1$, $R^2$, $R^3$, $R^4$, $R^5$ and $R^6$ are each as defined above, in the presence of a catalyst selected from the group consisting of a zeolite, a phosphate, phosphoric acid or boric acid on a carrier material, an acidic metal oxide and mixtures thereof.

2. The process of claim 1, wherein the catalyst used is an aluminosilicate, borosilicate or iron silicate zeolite of the pentasil type, a zeolite of the faujasite type or a mixture thereof.

3. The process of claim 1, wherein the catalyst used is a zeolite doped with an alkali metal, a transition metal, a rare earth metal or a mixture thereof.

4. The process of claim 1, wherein the catalyst used is a phosphate of one of the elements B, Al, Zr, Ce, Fe or Sr or a mixture thereof.

5. The process of claim 1, wherein the catalyst used is a hydrothermally synthesized phosphate having a zeolite structure.

6. The process of claim 1, wherein the catalyst used is a hydrothermally synthesized aluminum phosphate or silicon aluminum phosphate or silicon iron aluminum phosphate or boron aluminum phosphate.

7. The process of claim 1, wherein the catalyst used is phosphoric acid or boric acid on $SiO_2$, $Al_2O_3$, $TiO_2$ or pumice as a carrier material.

8. The process of claim 1, wherein the catalyst used is a metal oxide of one of the elements Al, Si, Ti, Zr, Be, Cr and V.

* * * * *

UNITED STATES PATENT AND TRADEMARK OFFICE
CERTIFICATE OF CORRECTION

PATENT NO. : 4,968,831

DATED : November 6, 1990

INVENTOR(S) : Norbert GOETZ et al.

It is certified that error appears in the above-identified patent and that said Letters Patent is hereby corrected as shown below:

Title page:

FOREIGN APPLICATION PRIORITY DATA

"March 15, 1989  DE   Fed. Rep. of Germany ...3808512"

should read

--March 15, 1988  DE   Fed. Rep. of Germany ...3808512--

Signed and Sealed this

Eighteenth Day of February, 1992

Attest:

HARRY F. MANBECK, JR.

Attesting Officer

Commissioner of Patents and Trademarks